(12) United States Patent
Thornton (10) Patent No.: US 8,998,944 B2
(45) Date of Patent: Apr. 7, 2015

(54) INVERTIBLE INTRAVASCULAR FILTER

(75) Inventor: Sally C. Thornton, Marlborough, MA (US)

(73) Assignee: Lifescreen Sciences LLC, Frisco, TX (US)

( * ) Notice: Subject to any disclaimer, the term of this patent is extended or adjusted under 35 U.S.C. 154(b) by 1916 days.

(21) Appl. No.: 10/865,017

(22) Filed: Jun. 10, 2004

(65) Prior Publication Data

US 2005/0277977 A1  Dec. 15, 2005

(51) Int. Cl.
*A61M 29/00* (2006.01)
*A61F 2/01* (2006.01)

(52) U.S. Cl.
CPC .............. *A61F 2/01* (2013.01); *A61F 2002/016* (2013.01); *A61F 2230/005* (2013.01); *A61F 2230/0067* (2013.01); *A61F 2230/0078* (2013.01)

(58) Field of Classification Search
CPC ........................................................ A61F 2/01
USPC .......... 606/200, 191, 194, 198; 623/1.15, 1.6, 623/1.16, 1.11
See application file for complete search history.

(56) References Cited

U.S. PATENT DOCUMENTS

| | | |
|---|---|---|
| 4,494,531 A | 1/1985 | Gianturco |
| 4,723,549 A | 2/1988 | Wholey et al. |
| 4,817,600 A | 4/1989 | Herms et al. |
| 5,152,777 A | 10/1992 | Goldberg et al. |
| 5,344,427 A | 9/1994 | Cottenceau et al. |
| 5,549,626 A | 8/1996 | Miller et al. |
| 5,626,605 A | 5/1997 | Irie et al. |
| 5,634,942 A | 6/1997 | Chevillon |
| 5,681,347 A | 10/1997 | Cathcart et al. |
| 5,720,764 A | 2/1998 | Naderlinger |
| 5,755,790 A | 5/1998 | Chevillon et al. |
| 5,800,457 A | 9/1998 | Gelbfish |
| 5,836,968 A | 11/1998 | Simon et al. |
| 5,853,420 A | 12/1998 | Chevillon et al. |
| 5,893,869 A | 4/1999 | Barnhart et al. |
| 5,947,995 A | 9/1999 | Samuels |
| 5,954,741 A | 9/1999 | Fox |
| 5,976,172 A | 11/1999 | Homsma et al. |
| 6,007,558 A | 12/1999 | Ravensoft et al. |
| 6,013,093 A | 1/2000 | Nott et al. |
| 6,059,825 A | 5/2000 | Hobbs et al. |
| 6,126,673 A | 10/2000 | Kim et al. |
| 6,193,739 B1 | 2/2001 | Chevillon et al. |
| 6,214,025 B1 | 4/2001 | Thistle et al. |
| 6,231,589 B1 | 5/2001 | Wessman et al. |
| 6,241,746 B1 | 6/2001 | Bosma et al. |

(Continued)

*Primary Examiner* — Katherine M Shi
(74) *Attorney, Agent, or Firm* — Seager, Tufte & Wickhem LLC (57) ABSTRACT

An intravascular filter for use in a body vessel lumen having a longitudinal axis, which may include a plurality of elongate filter members, each of the plurality having a first portion and having a first end and a second end, a plurality of anchoring members, each of the plurality of anchoring members joint to a first end of an elongate filter member, and a filter center portion, each elongate filter member second end joined to the filter center portion, wherein the plurality of elongate filter member first portions may extend radially outward and in a first longitudinal direction when the intravascular filter is disposed in the body vessel lumen, and wherein when the intravascular filter may be disposed in the body vessel lumen, the plurality of elongate filter member first portions are adapted to be moved from extending radially outward and in the first longitudinal direction to extending radially outward and in the second longitudinal direction.

13 Claims, 10 Drawing Sheets

(56) References Cited

U.S. PATENT DOCUMENTS

| | | | |
|---|---|---|---|
| 6,258,026 B1 | 7/2001 | Ravensoft et al. | |
| 6,267,776 B1 | 7/2001 | O'Connell | |
| 6,306,163 B1 | 10/2001 | Fitz | |
| 6,342,062 B1 | 1/2002 | Suon et al. | |
| 6,391,045 B1 | 5/2002 | Kim et al. | |
| 6,409,742 B1 * | 6/2002 | Fulton et al. | 606/200 |
| 6,416,530 B2 | 7/2002 | DeVries et al. | |
| 6,436,120 B1 | 8/2002 | Meglin | |
| 6,468,290 B1 * | 10/2002 | Weldon et al. | 606/200 |
| 6,517,559 B1 | 2/2003 | O'Connell | |
| 6,582,447 B1 | 6/2003 | Patel et al. | |
| 6,652,558 B2 | 11/2003 | Patel et al. | |
| 6,706,054 B2 | 3/2004 | Wessman et al. | |
| 2002/0045917 A1 | 4/2002 | Ambrisco et al. | |
| 2002/0111647 A1 * | 8/2002 | Khairkhahan et al. | 606/200 |
| 2002/0193825 A1 | 12/2002 | McGuckin et al. | |
| 2002/0193827 A1 | 12/2002 | McGuckin et al. | |
| 2002/0193828 A1 | 12/2002 | Griffin et al. | |
| 2003/0139765 A1 | 7/2003 | Patel et al. | |
| 2004/0158274 A1 * | 8/2004 | WasDyke | 606/200 |
| 2004/0193209 A1 * | 9/2004 | Pavcnik et al. | 606/200 |

* cited by examiner

INVERTIBLE INTRAVASCULAR FILTER

FIELD OF THE INVENTION

The present invention relates generally to devices for filtering blood clots within a blood vessel. More specifically, the present invention pertains to intravascular filter devices and associated methods for deploying such devices within the body.

BACKGROUND OF THE INVENTION

Intravascular filters may be used in combination with other thrombolytic agents to treat pulmonary embolism occurring within a patient. Such devices are generally inserted intravenously into a target location of the body (e.g. an artery or vein), and function by capturing blood clots (emboli) contained in the blood stream before they can reach the heart and/or lungs and cause permanent damage to the body. In the treatment of Deep Vein Thrombosis (DVT), for example, such filters can be placed in the vena cava to prevent further blood clotting in the large veins of the lower body. Placement of the filter is typically accomplished percutaneously via the femoral arteries or the jugular vein using a local anesthetic, or by performing a laparotomy with the patient under general anesthesia.

Intravascular filters are typically preloaded into an introducer sheath and are packaged and stocked in this preloaded configuration. Intravascular filters typically have a wide mouth that narrows to an apex. This apex generally needs to be located downstream of the mouth for the filter to function effectively. Thus the filter needs to be preloaded in the introducer sheath in the proper configuration. This configuration is often different depending on whether a femoral or jugular approach is used. Thus, two distinct preloaded systems with the same filter need to be stocked, one for each approach. It thus may be desirable to develop a filter which can be properly oriented after it is in the body lumen.

SUMMARY OF THE INVENTION

One embodiment pertains to an intravascular filter having an apical head operatively coupled to a number of elongate filter legs that can be expanded within a blood vessel to collect any emboli which may be in the blood stream. The apical head may include a ball or other member which can be grasped and the elongate filter legs are jointed. At the end of the elongate filter legs are anchoring members which may be used to retain the filter to the wall and are suitable in either configuration. In use, the filter is deployed into a blood vessel and expanded in a first orientation. The anchoring members may attach to the vessel wall at this point. If a second orientation is desired, the apical head is grasped and pulled to invert the filter.

Another embodiment pertains to an intravascular filter having an apical head operatively connected to a number of elongate filter legs. The apical head may be an extension of one of the elongate filter legs, with the other filter legs slidably connected to the apical head. The apical head may include a ball or other member which can be grasped to invert the filter when desired.

Another embodiment pertains to an intravascular filter having a number of v-shaped wires woven together at the angle to form a cone-shaped filter. A number of retaining members may be pivotably attached to the ends. The filter is configured so that if one of the wires is grasped at the apex and pulled, the filter may be inverted.

Anther embodiment pertains to an intravascular filter having an apical head and a number of elongate members attached thereto to form a cone shaped filter. A number of anchoring members may be pivotably attached to the elongate members. The apical head may be grasped and pulled to invert the filter.

The above summary of some embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which.

DETAILED DESCRIPTION OF ILLUSTRATIVE EMBODIMENTS

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
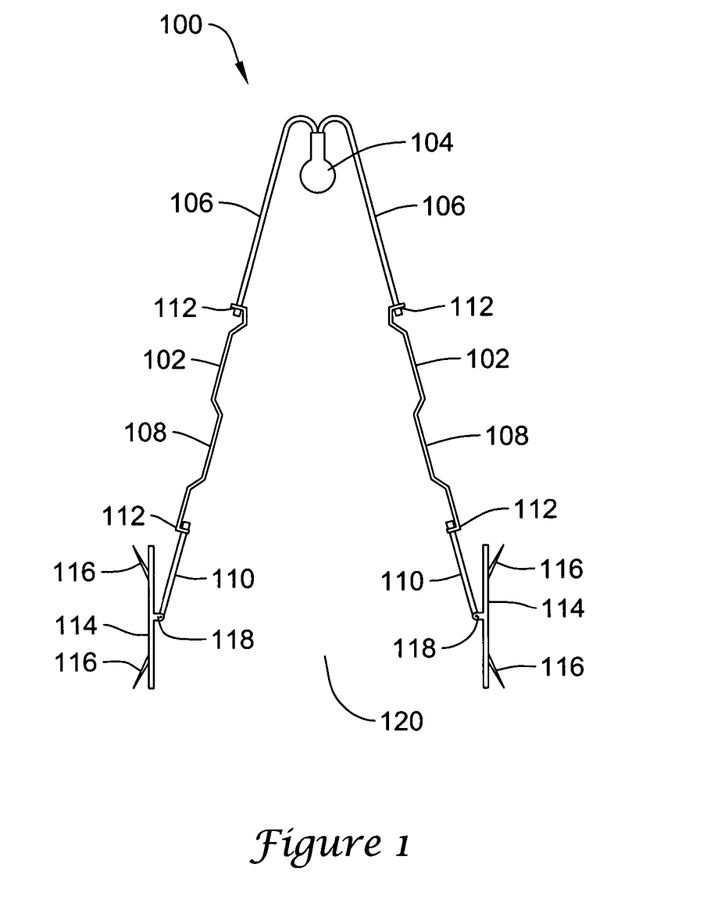
FIG. 1 is a diagrammatic view of a filter 100 in a first position.

FIG. 1 is a diagrammatic view of an implantable intravascular filter 100 in a first position. Filter 100 is depicted as a vena cava filter though it could be any intravascular filter. Filter 100 includes an apical head 104 connected to a number of filter legs 102 each having a first segment 106, a second segment 108, and a third segment 110. In this diagrammatic view only two filter legs are pictured. However, more filter legs are usually included. For example, most Greenfield type vena cava filters have six filter legs, although more or fewer legs may be used. For example, a filter may have five or eight legs. Legs 102 are generally disposed symmetrically about a central longitudinal axis of the filter. Legs 102 are biased to extend outwardly from apical head 104 to generally form a cone shape.

Segments 106 and 108, and 108 and 110 are joined at joints 112 to form legs 102. Joints 112 may permit sliding or rotation of the segments with respect to each other. For example, in the embodiment depicted, joints 112 permit sliding of segments 108 over segments 106 and segments 110. Joints 112 may have a ball or taper which fit into a loop of an adjacent segment. Of course, other configurations are contemplated. For example, the male portions of the joints may be on segment 108 rather than on segments 106 and 110. In another configuration, the joint may consist of a loop on each adjacent segment, which each segment passing through the other's loop. Any joint that provides the desired degrees of freedom may be suitable.

Apical head 104 may be configured to be detachable from an elongate member (not pictured). For example, apical head 104 is bulbous and may be suitable for use with an elongate member having a noose or a hook that fits around the bulb. Other suitable readily detachable configurations include a hook and eye configuration, a screw and threaded hole configuration, and an electromagnetic configuration. Alternatively, filter legs may be joined to each other and the apical head may be omitted. An elongate member having a hook may be suitable for releasably engaging the apex of this configuration.

Engagement members 114 may be mounted to filter legs 102. Engagement members 114 are configured to engage the walls of a body vessel lumen to prevent movement of the filter, and may have barbs 116. A first barb 116 may be pointed in a first longitudinal direction and a second barb 116 may be pointed in a second longitudinal direction opposite the first. Each engagement member 116 may include an elongate region that lies against the wall of a body vessel lumen. This elongate region may be a portion of a wire or may be planar. Engagements members 116 may be connected to filter legs 102 through joints 118, which may be pivotable, rotatable or flexible.

Filter 100 may be made from a metal such as stainless steel or a nickel titanium alloy. Other metals which may be suitable to use in the filter in whole or part include gold, tantalum, tungsten, titanium, Beta III Titanium, Nitinol, a cobalt cromium alloy, Elgiloy, L605, MP35N, Ta-10W, 17-4PH, or Aeromet 100. Certain polymers such as thermosets or thermopolymers may be suitable as well. In general filter legs 102 and in particular segments 106 should be flexible and resilient. The filter legs may be formed from a wire, rod, tubing or other structure that can be processed to form the structures shown.

Figure 2:
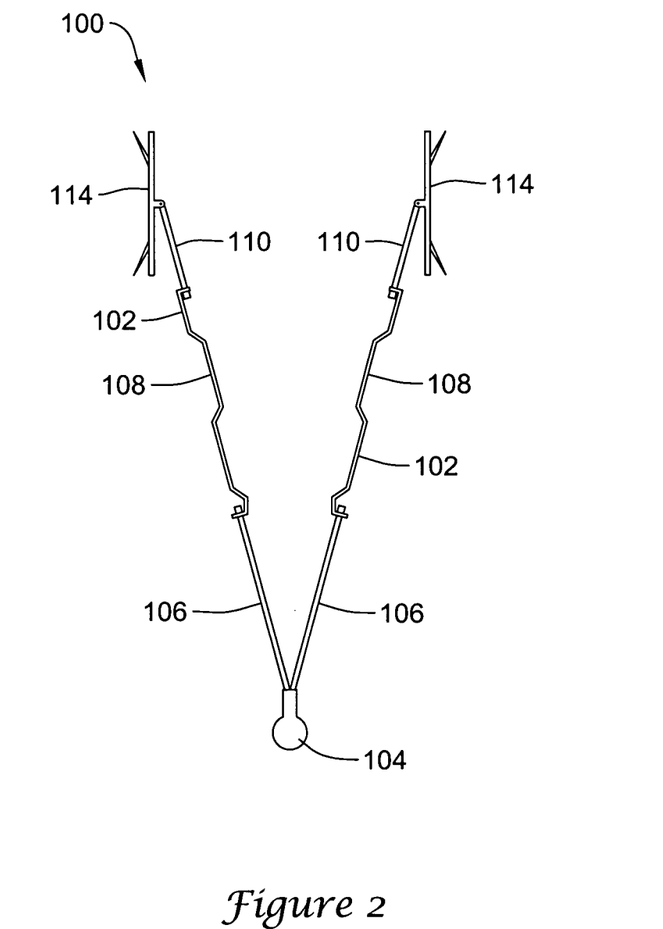
FIG. 2 is a diagrammatic view of filter 100 in a second position.

FIG. 1 is a schematic view of filter 100 in a first position and FIG. 2 is a schematic view of the filter in a second position. Although in both figures, the filter alone is depicted, both positions may be confined positions. In general, one may move the filter from the first position to the second position by the following process, a process that will be described in further detail herein below with respect to another embodiment. The filter is deployed from a catheter into a body vessel lumen and thereupon assumes position 1. An elongate member is detachably engaged with apical head 104. If desired to move filter 100 to position 2, the apical head is pulled through filter mouth 120 of the filter. Because the filter has been deployed and is engaged with the vessel wall through engagement members 114, the filter will tend to stay in place. As the filter is being pulled, segments 106, 108, and 110 may slide in on each other, reducing the length of filter legs 102. Filter legs 102 may tend to bend as well, and the reduced length may lessen the pressure on the vessel wall. Apical head 104 is pulled through filter mouth 120 and may be pulled still further until the filter legs are fully extended and the filter is inverted as shown in FIG. 2. Filter legs 102 may rotate on anchoring members 114 about joints 118. The elongate member may then be disengaged from the apical head. Segments 106 may be curved as shown in FIG. 1 in position 1 proximate the apical head, but may be biased to be substantially straight. This curve, while insufficient to alter the position of the filter by itself, may be helpful in inverting the filter.

Figure 3:
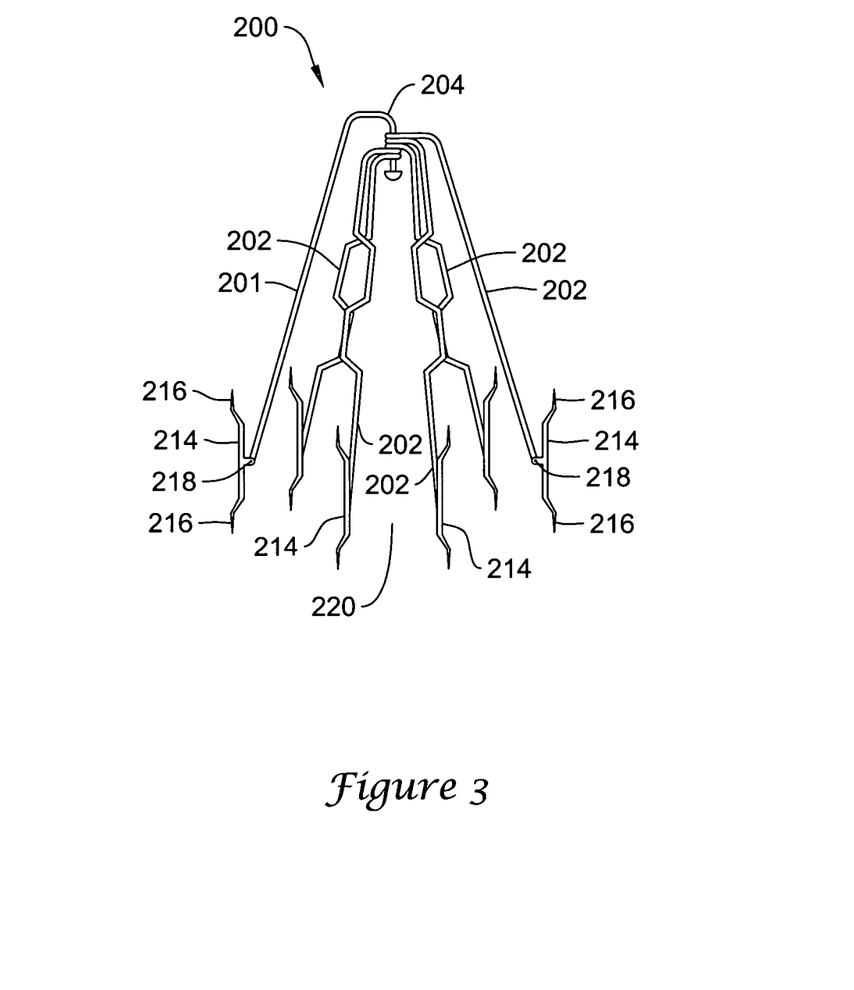
FIG. 3 is a perspective view of a filter 200 in a first position.

FIG. 3 is a perspective view of a filter 200 in a first position. A first leg 201 terminates at apical head 204, to which remaining legs 202 are slidably attached. Apical head 204 includes suitable structure for being releasably attached to an elongate member. Suitable structure has been described above. Legs 201 and 202 may be attached to anchoring members 214, which may include barbs 216 for engagement with the vessel wall. The attachment between the legs and anchoring members may be with pivotable joints 218. Legs 201 and 202 are generally radially disposed about a central axis as shown to form the filter. While six legs are shown, other numbers of legs, for example seven, may be suitable. In an alternative embodiment, filter leg 201 does not terminate at the apical head. Rather, all the filter legs are slideably attached to an apical head that extends for a length to allow room for sliding and which is configured so no leg can slide off the apical head.

Figure 4:
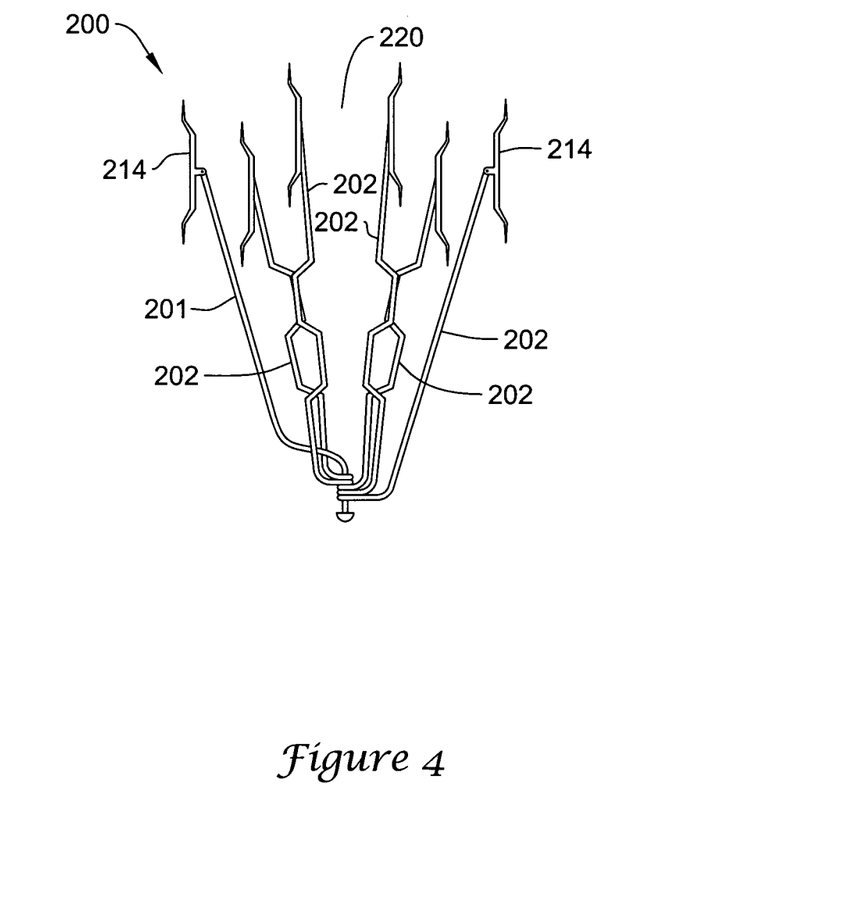
FIG. 4 is a perspective view of filter 200 in a second position.

Filter 200 may be deployed into a body vessel lumen in position 1 as shown in FIG. 1. Anchoring members 214 may engage the wall of the body vessel. If desired, an elongate member may be attached to apical head 204 to pull apical head 204 through filter mouth 220 to invert the filter. Legs 202 are free to slide along apical head 204 and leg 201 during this inversion process but are biased to return to the shapes shown in the figures.

Figure 5:
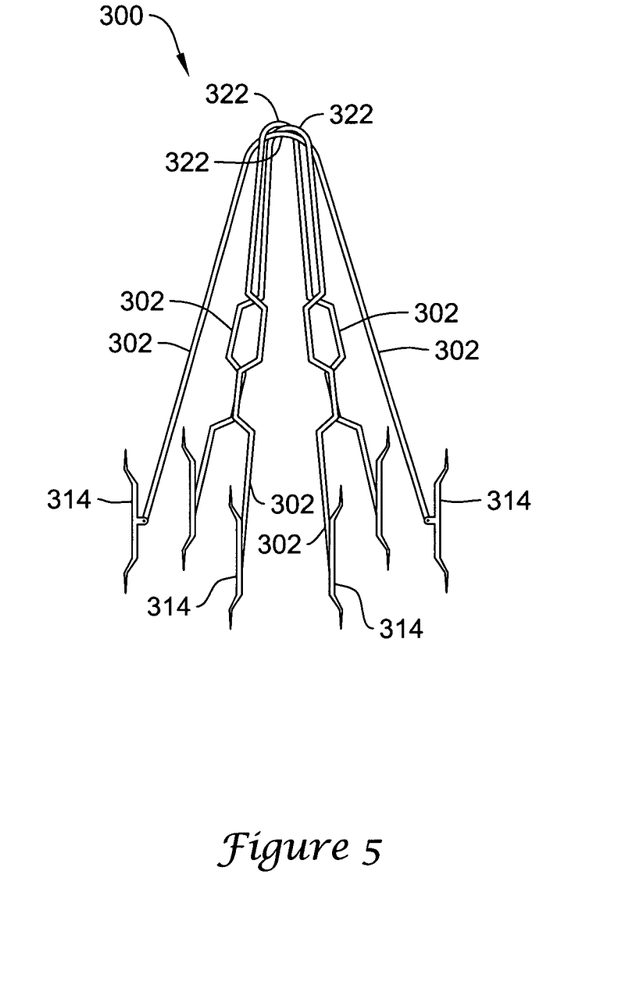
FIG. 5 is a perspective view of a filter 300 in a first position.

FIG. 5 is a perspective view of a filter 300. Filter 300 includes an even number of filter legs 302. FIG. 5 depicts six filter legs, but other numbers may be suitable such as eight or ten. Each pair of filter legs is joined together at a first end with a bend 322 to form a v-shaped or u-shaped member. The pairs of filter legs are then interwoven in the manner shown in the figure or in another suitable fashion such that if any bend is grasped with a grasper such as a hook on an elongate member and pulled to invert, the other bends (and corresponding filter legs) follow. Each leg may also be attached to an anchoring member 314 in a manner as described herein above. In an alternative embodiment, a loop or other structure may be positioned on one or more of the bends to facilitate grasping.

Figure 6:
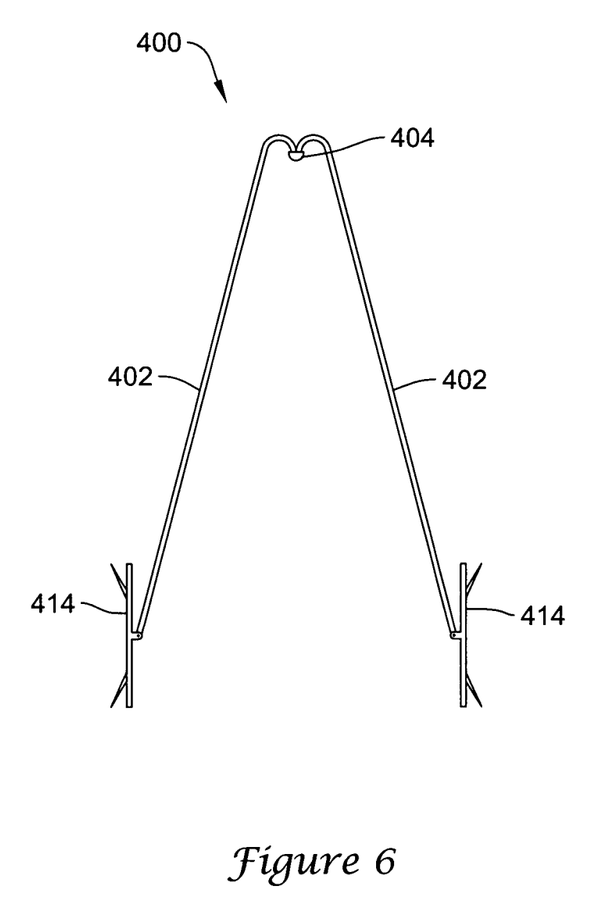
FIG. 6 is a diagrammatic view of a filter 400 in a first position.
Figure 7:
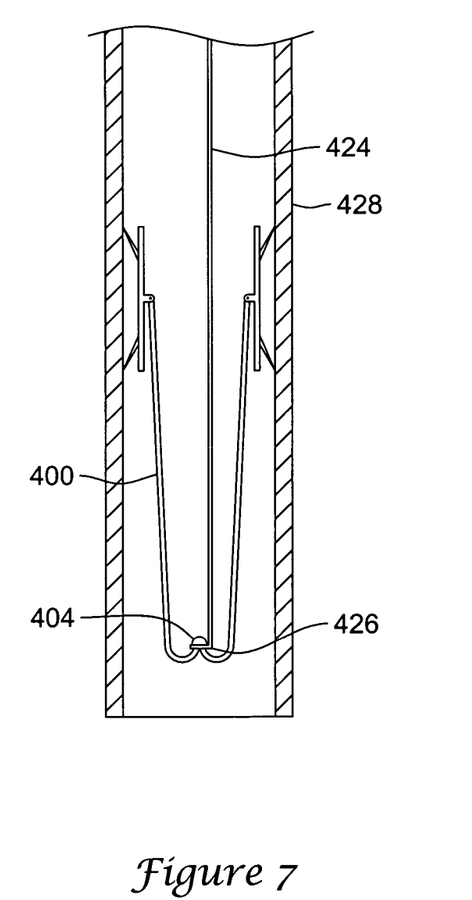
FIG. 7 is a diagrammatic view of filter 400 in a catheter.

FIG. 6 is a diagrammatic view of a filter 400 in a first position, which includes filter legs 402 attached to an apical member 404 and to anchoring members 414 as shown. Filter legs 402 may be highly flexible and resilient and may be biased to be substantially straight. Only two legs are depicted, but more legs are contemplated. For example, filter 400 may include five, six or seven legs disposed symmetrically about a central axis. Filter 400 may include a filtering mesh or membrane (not shown) attached to the legs. In FIG. 7, which is a diagrammatic view, filter 400 is shown loaded in a catheter 428. An elongate member 424 is releasably attached to apical head 404 by hook 426 which fits over the apical head. In one alternative, apical member has a male thread which fits and is threaded into a threaded hole at the end of the elongate member. Other suitable apical heads and attachment members are contemplated.

Figure 8:
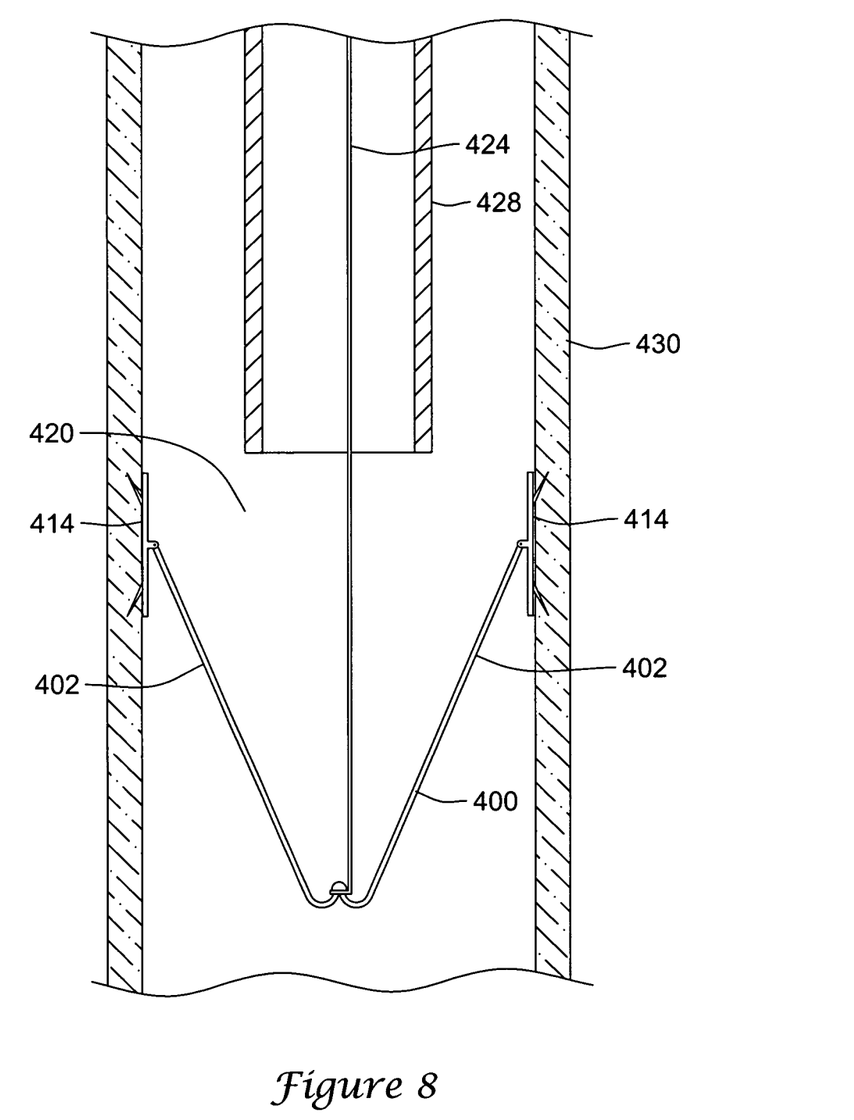
FIG. 8 is a diagrammatic view of filter 400 in a body vessel lumen.

The catheter is advanced to a desired filter placement location in a body vessel lumen and deployed from the catheter lumen as shown. This deployment may be done by retracting the catheter to allow the filter legs to spring outward or may be done by advancing the filter from the catheter lumen by pushing with elongate member 424 or another device. Anchoring members 414 engage the vessel wall 430. If the filter mouth 420 is facing in the desired direction, elongate member 424 may be disengaged from the filter and retracted.

Figure 9:
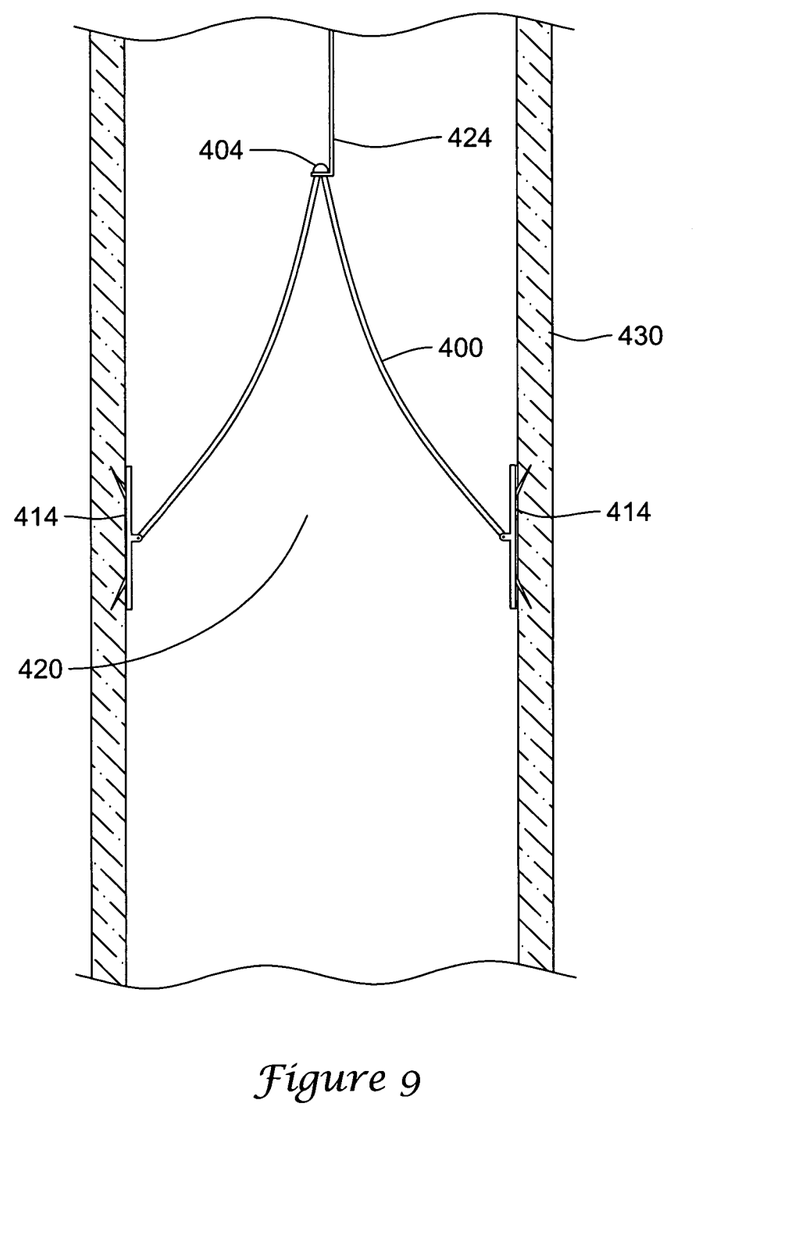
FIG. 9 is a diagrammatic view of filter 400 in a body vessel lumen.
Figure 10:
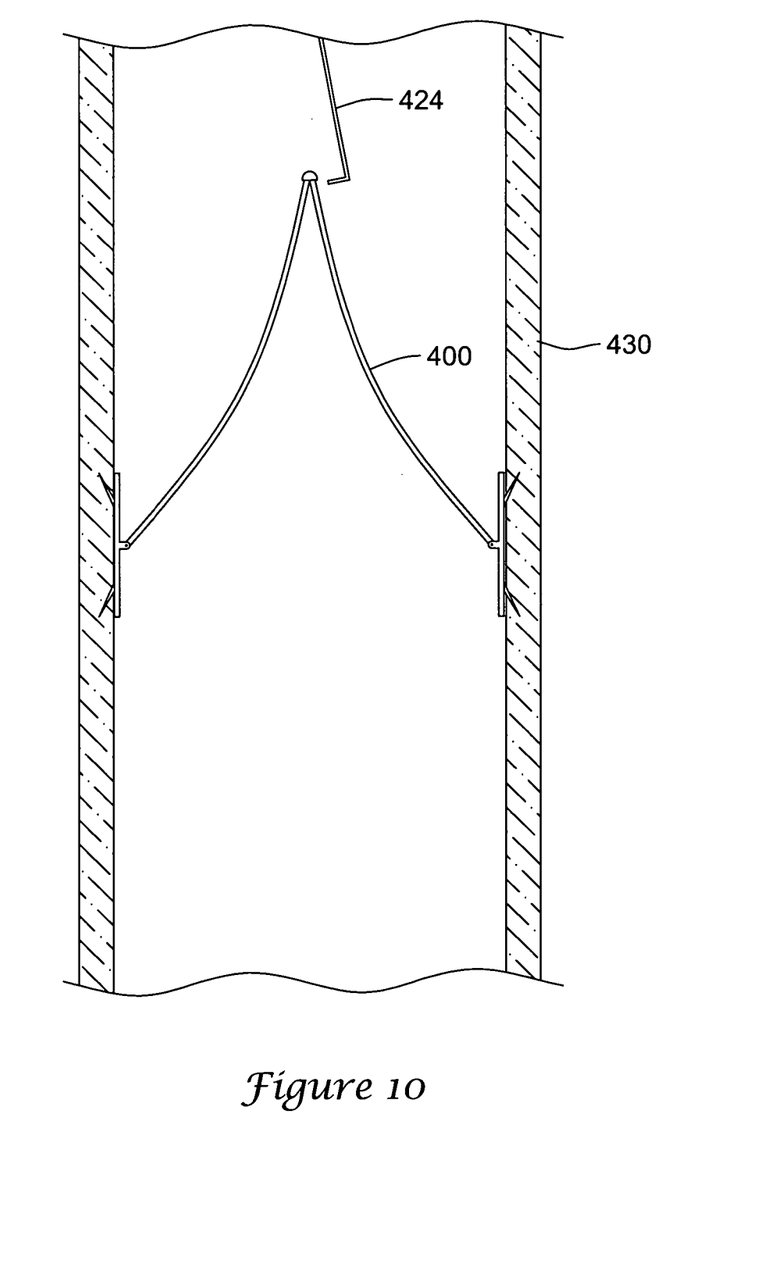
FIG. 10 is a diagrammatic view of filter 400 in a body vessel lumen.

If inversion is desired, elongate member may be operated to pull apical head 404 through filter mouth 420 so that the filter is in a second position as shown in FIG. 9. The first position may be desired if the blood is flowing in a first direction and the second position may be desired if the blood is flowing in a second direction. Thus, the same filter loading configuration may be used for both a radial and femoral approach, for example. When the filter is in the desired position, elongate member 424 may be disengaged from the filter and retracted, as shown in FIG. 10.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An invertible vena cava filter, comprising:
   an apical head;
   a plurality of filter legs extending from the apical head in a first generally axial direction in a first configuration, wherein each of the filter legs includes a first segment, a second segment slidably and rotatably joined at a joint to the first segment, and a third segment slidably and rotatably joined at a joint to the second segment; and
   wherein each segment has a first end toward the apical head and a second end toward the first generally axial direction, and the first end of the second segment is joined to the second end of the first segment and the first end of the third segment is joined to the second end of the second segment;
   wherein each of the filter legs includes an engagement member attached to the second end of the third segment, the engagement member including one or more barbs;
   wherein, while the engagement members are disposed at a fixed radius generally corresponding to the radius of the vena cava, a force applied to the apical head in the first axial direction urges the joints joining the first and second segments and the joints joining the second and third segments to rotate and slide cooperatively to allow the apical head to pass the engagement members axially whereupon the plurality of filter legs assume a second configuration in which said legs extend from the apical head in a second generally axial direction wherein the first and second axial directions are opposed.

2. The invertible vena cava filter of claim 1, wherein the invertible vena cava filter includes two filter legs.

3. The invertible vena cava filter of claim 1, wherein the invertible vena cava filter includes six filter legs.

4. The invertible vena cava filter of claim 1, wherein the invertible vena cava filter includes five to eight filter legs.

5. The invertible vena cava filter of claim 1, wherein the second segment is slidably and rotatably joined at a joint to the first segment with a ball and loop joint.

6. The invertible vena cava filter of claim 1, wherein the second segment is slidably and rotatably joined at a joint to the first segment with a taper and loop joint.

7. The invertible vena cava filter of claim 1, wherein the second segment is slidably and rotatably joined at a joint to the first segment by connecting a first loop disposed on the first segment to a second loop disposed on the second segment.

8. The invertible vena cava filter of claim 1, wherein the engagement member is rotatably joined at a joint to the third segment.

9. The invertible vena cava filter of claim 1, wherein the engagement member is pivotably joined at a joint to the third segment.

10. The invertible vena cava filter of claim 1, wherein the engagement member includes a first barb pointed in a first direction and a second barb pointed in a second direction that is substantially opposite the first direction.

11. The invertible vena cava filter of claim 1, wherein the invertible vena cava filter is configured to shift between a first configuration where the engagement members on each of the filter legs is disposed on a first side of the apical head and a second configuration where the engagement members on each of the filter legs is disposed on a second side of the apical head which is opposite the first side.

12. An invertible vena cava filter, comprising:
    a filter head;
    a plurality of filter legs extending from the head in a first generally axial direction in a first configuration, wherein each of the filter legs includes a first segment, a second segment slidably and rotatably joined at a joint to the first segment, a third segment slidably and rotatably joined at a joint to the second segment, and an engagement member attached to the third segment; and
    wherein each segment has a first end toward the apical head and a second end toward the first generally axial direction, the first end of the second segment is joined to the second end of the first segment, the first end of the third segment is joined to the second end of the second segment, and the engagement member is attached to the second end of the third segment;
    wherein the invertible vena cava filter is configured to shift between a first configuration where the filter legs are oriented in a first generally axial direction and a second configuration where the filter legs are oriented in a second generally axial direction that is substantially opposite the first direction upon application of a force to the head in the first generally axial direction;
    wherein the engagement members of the plurality of legs remain disposed at a radius substantially equal to the radius at which they are disposed in the first configuration during the transition between the first configuration and the second configuration.

13. An invertible vena cava filter, comprising:
    a filter head;
    a plurality of filter legs extending from the head in a first generally axial direction in a first configuration, wherein each of the filter legs includes a first segment, a second segment slidably and rotatably joined at a joint to the first segment, a third segment slidably and rotatably joined at a joint to the second segment, and an engagement member attached to the third segment; and
    wherein each segment has a first end toward the apical head and a second end toward the first generally axial direction, the first end of the second segment is joined to the second end of the first segment, the first end of the third segment is joined to the second end of the second segment, and the engagement member is attached to the second end of the third segment;
    wherein the invertible vena cava filter is configured to shift between a first configuration where the engagement members on the plurality of filter legs are disposed in a first generally axial direction relative to the head and a second configuration where the engagement members on the plurality of the filter legs are disposed on a second side of the head opposite the first side;
    further wherein the engagement members of the plurality of legs remain disposed at a radius substantially equal to the radius at which they are disposed in the first configuration during the transition between the first configuration and the second configuration.

* * * * *